(12) United States Patent
Watanabe et al.

(10) Patent No.: US 6,808,380 B1
(45) Date of Patent: Oct. 26, 2004

(54) HARDNESS TAPER TUBE AND PRODUCTION METHOD AND DEVICE THEREFOR

(75) Inventors: Yukio Watanabe, Shizuoka (JP); Takeshi Kizuka, Shizuoka (JP)

(73) Assignee: GMA Co., Ltd., Shizuoka (JP)

( * ) Notice: Subject to any disclaimer, the term of this patent is extended or adjusted under 35 U.S.C. 154(b) by 0 days.

(21) Appl. No.: 10/019,658

(22) PCT Filed: Oct. 13, 2000

(86) PCT No.: PCT/JP00/07108
§ 371 (c)(1),
(2), (4) Date: Jan. 2, 2002

(87) PCT Pub. No.: WO01/89802
PCT Pub. Date: Nov. 29, 2001

(30) Foreign Application Priority Data

May 26, 2000 (JP) .................................... 2000-157212

(51) Int. Cl.[7] ............................................. B29C 47/00
(52) U.S. Cl. .................... 425/131.1; 425/208; 425/209; 425/381; 425/467; 366/90; 366/322
(58) Field of Search ................ 366/90, 322; 425/131.1, 425/132, 208, 209, 380, 381, 467, 381.2, 382.3

(56) References Cited

U.S. PATENT DOCUMENTS

| | | | | |
|---|---|---|---|---|
| 3,502,752 A | * | 3/1970 | Brown ....................... 264/412 |
| 3,642,396 A | * | 2/1972 | Meneidis .................. 425/133.1 |
| 3,752,617 A | | 8/1973 | Burlis et al. ............. 425/131.1 |
| 3,913,897 A | * | 10/1975 | Hanslik ...................... 366/88 |
| 4,045,401 A | | 8/1977 | Stenmark et al. ........... 523/324 |
| 4,250,072 A | | 2/1981 | Flynn ......................... 524/288 |
| 5,318,357 A | * | 6/1994 | Colby et al. .................. 366/81 |
| 5,533,985 A | | 7/1996 | Wang ......................... 604/264 |
| 5,622,665 A | | 4/1997 | Wang ......................... 264/150 |
| 5,843,503 A | * | 12/1998 | Clanton et al. ............. 426/249 |
| 6,059,769 A | | 5/2000 | Lunn et al. ................. 604/523 |

FOREIGN PATENT DOCUMENTS

| | | |
|---|---|---|
| GB | 2 178 691 A | 2/1987 |
| JP | 51-79048 | 7/1976 |
| JP | 52-48150 | 1/1977 |
| JP | 54-8036 | 4/1979 |
| JP | 62-19427 | 1/1987 |
| JP | 2-131738 | 5/1990 |
| JP | 2-280765 | 11/1990 |
| JP | 5-23398 | 2/1993 |

* cited by examiner

Primary Examiner—Robert Davis
Assistant Examiner—Joseph S Del Sole
(74) Attorney, Agent, or Firm—Finnegan, Henderson, Farabow, Garrett & Dunner, LLP

(57) ABSTRACT

An apparatus for manufacturing stiffness-taper tubing includes a die having an extrusion hole, a die holder for holding the die, and a mandrel mounted inside the die holder and that fits in the extrusion hole. The apparatus forms stiffness-taper tubing by switching between and supplying resins having different stiffnesses over the mandrel from a plurality of resin-supply ports formed in the die holder such that the stiffness gradually changes in the lengthwise direction. A mandrel insertion hole connecting to the extrusion hole is formed in the die holder and the mandrel is mounted in this mandrel insertion hole. The plurality of resin-supply ports open to a cylindrical space formed between the inner surface of the mandrel insertion hole and the outer surface of the mandrel at a position separated from the extrusion hole in the die, and the plurality of resins flow together in this space.

3 Claims, 6 Drawing Sheets

A – A

HARDNESS TAPER TUBE AND PRODUCTION METHOD AND DEVICE THEREFOR

TECHNICAL FIELD

This invention relates to stiffness-taper tubing, that is formed by joining two or more resin materials having different stiffness such that the stiffness along its length gradually changes, and to the manufacturing method and manufacturing apparatus for such tubing. The stiffness-taper tubing of this invention is suitable for use in medical applications such as a catheter.

BACKGROUND ART

Conventionally, a two-layer extrusion-type formation apparatus was used when using two types of resin materials having different stiffness to form stiffness-taper tubing. The stiffness-taper tubing was formed such that there was a stiff section made from a first resin, having much stiffness in the longitudinal direction, a soft section made from a second resin, having little stiffness, and a transition section between these two sections in which the stiffness gradually changed (stiffness taper section). For this kind of stiffness-taper tubing, the first resin and then the second resin is supplied to the two-layer extrusion-type formation apparatus, and the transition section is formed when switching between resins and the first resin is gradually replaced by the second resin.

When this kind of stiffness-taper tubing is used in medical applications such as a catheter, a joint between both resin materials in the transition section that is adequately strong is required, and it is desired that the length of the transition section be long enough to be able to maintain its function as a catheter, but also be as short as possible in order to improve operability.

FIG. 7 is a horizontal cross-sectional diagram of a two-layer extrusion-type formation apparatus that the inventors used before developing the present invention.

This two-layer extrusion-type formation apparatus 30 comprises a die having an extrusion hole 31, a die holder 34 for holding the die by way of a bolt 33, and a mandrel 35 that is mounted such that it faces the extrusion hole 31. The mandrel 35 is attached to and held by the die holder 34 by way of an inner-layer mandrel holder 36 and outer-layer mandrel holder 37. The inner-layer and outer-layer mandrel holders 36, 37 are nearly conical shaped, and there is a guide cavity 38 formed all the way around the tip of the cone for supplying resin to the mandrel 35.

On both of the outer sides of the die holder 34 there are switching devices 39, 49 for switching between and supplying the different types of resins A and B. The switching devices 39, 40 are connected respectively to the resin A supply port 43 and resin B supply port 45, that are located on the die holder 34. There are heaters 47 on the die holder 34 and switching devices 39, 40 for keeping the resins soft.

The switching device 39 for supplying resin A comprises a switching valve 41, and a resin A inlet 42 that is connected to the resin A extruder. Resin A is supplied to the resin A supply port 43 on the die holder 34 as the switching valve 41 turns. The resin A, that is supplied to the resin A supply port 43, is supplied to a channel 49 in the outer-layer mandrel holder 37 by way of a connection path 44, and then supplied to the guide cavity 38 on the tip by way of this channel 49 and drawn out from the extrusion hole 31 by way of a ring-shaped space on the outer surface of the mandrel 35.

Similarly, resin B passes through the resin B supply port and connection path 46 and is supplied to the guide cavity 38 by way of the channel 49 in the inner-layer mandrel holder 36, and then is drawn out from the extrusion hole 31 by way of the ring-shaped space on the outer surface of the mandrel 35.

When either resin A or resin B is selected by the switching device 39, 40 and supplied to the die holder 34, the resin that is not selected passes through the switching valve 41 of the respective switching device 39 or 40 and is discharged through the resin discharge port (not shown in the figure). At that time, part of the resin that was not selected remains in the resin supply ports 43, 45 of the switching devices 39, 40 and the die holder 34, in the connection paths 44, 46, in the channels in the inner-layer and outer-layer mandrel holders 36, 37 and in the guide cavity 38, and remains there until the resin is switched and fed again.

The mandrel 35 is fastened to the end of a shaft 48. The center axis of this shaft 48 is coaxial with the center axis of the extrusion hole 31 in the die 32. This shaft 48 is fastened to and held inside the die holder 34 by fastening it on the inside of the inner-layer mandrel holder 36. During use, a core member passes along the axis of, for example the shaft 48, mandrel 35 and extrusion hole 31, and melted resin, that was selected by the switching device, is supplied from the extrusion hole 31 and flows around this core member to form tubing.

In this kind of two-layer extrusion-type formation apparatus 30, two kinds of resin are mixed at the point C in the figure where the respective cavity 38 opens up to the conical-shaped inlet of the extrusion hole 31 in the die 32, and the mixed resin is discharged in a formed shape from the outlet of the extrusion hole 31 at point D in the figure. Moreover, when the two kinds of resins are alternately switched and supplied to the die 32, at the time of switching, the first resin fills the space from the extrusion hole 31, between the mixing point C at the die inlet and it the discharge point D at the die outlet, and the mandrel 35. The resin that fills the space between this mixing point C and discharge point D is then replaced by the next resin after switching. The transition section becomes the part from the start of replacement to the end of replacement.

However, in the inventor's prior 2-layer extrusion-type device, the cavities 38 for both the inner-layer 36 and outer layer 37 open up at the mixing point C, so the volume between this mixing point C and discharge point D becomes large, and as a consequence the length of the transition section becomes long.

The length of the transition section is proportional to the time required for resin replacement. By taking the volume between the mixing point C and the discharge point D (called the joint-flow volume below) to be V, and taking the inflow rate of resin B, when going from 100% resin A to 100% resin B in this joint-flow volume V to be q, then the time T required for replacement is given by the following equation:

$$T = V/q + T1$$

(T1 is a constant that is determined by the mixing efficiency of resin A and resin B.) Moreover, the time T required for replacement becomes longer as the joint-flow volume V becomes larger. In other words, when the joint-flow volume V is large, the time T required for replacement becomes long and the length of the transition section becomes long in accordance.

Furthermore, in the prior two-layer extrusion-type formation apparatus, the resin supply path from the respective supply ports 43, 45 for resin A and resin B to the mixing point C becomes long and its volume becomes large. In addition, the amount of resin that remains in the resin supply path during switching becomes large, and while waiting, this residual resin is heated by the heaters and there is a possibility that its quality could be altered or become degraded.

Moreover, when forming stiffness-taper tubing with the prior two-layer extrusion-type formation apparatus, the second resin is supplied such that it pushes the residual first resin when the resin is switched, so there is hardly any mixing between the two resins at the interface between them, and the tubing is formed with a clear interface (contact plane) between the two resins. The two resins are joined with the two resins in contact with each other through this kind of distinct interface, so it is not possible to obtain adequate bonding strength, and there is the possibility that the tubing will come apart at the joint surface in the transition section.

On the other hand, a catheter having a transition section in which the stiffness changes from a rigid section to a soft section has been disclosed in U.S. Pat. No. 5533985, U.S. Pat. No. 5622665 and Japanese Pat. No. H9-512445. In the transition section of the catheter in these disclosures, an interface with a wedge-shaped cross section is formed by switching between two resin materials such that the first resin bites into the later resin. This kind of wedge-shaped contact surface was formed probably due to the fact that there is very little mixing between the two resins at the interface. When the two resins are joined with this kind of surface contact, it is not possible to obtain adequate bonding strength, and there is the possibility that the tubing will come apart at the wedge-shaped joint surface in the transition section.

DISCLOSURE OF THE INVENTION

Taking the above problems into consideration, the object of this invention is to provide stiffness-taper tubing and a manufacturing method and apparatus for such, in which the bonding strength in the transition section between resins having different stiffness is increased, and where the length of the transition section is shortened in order to maintain the function of the tubing to meet the conditions of use and improve operability, and furthermore where the volume of residual resin when switching resins is reduced as well as the degradation of the quality of residual resin due to heating is suppressed.

In order to accomplish the aforementioned objectives, the present invention provides stiffness-taper tubing in which at least a first resin and second resin, having differing stiffness, are joined such that the stiffness of the tubing gradually changes in the longitudinal direction, and where simple surface contact in a transition section between the first resin and second resin is broken and a section where both resins are uniformly mixed is formed.

With this structure, by extruding and replacing resin while at the same time mixing both resins when switching the two kinds of resins in forming a transition section, a section where simple surface contact in a transition section between the first resin and second resin is broken and a section where both resins are uniformly mixed is formed and the bonding strength is increased.

Simple surface contact is generally contact between flat or curved surfaces. Moreover, the section where both resins are uniformly mixed is not only a state of completely uniform mixture, but includes a state where an identifiable interface such as an inclined surface or wedge-shaped interface is broken down to some extent and both resins are alternately scattered.

Moreover, this invention provides a method of manufacturing stiffness-taper tubing which uses an extrusion mold comprising a die having and extrusion hole, a die holder for holding this die, and a mandrel that is mounted in this die holder and which fits inside the extrusion hole; and where the tubing is formed such that the stiffness changes gradually and continuously in the longitudinal direction by using a first resin and second resin that have different stiffness, and where the first resin and second resin are mixed in a cylindrical space that is formed between the die holder and mandrel.

With this structure, both resins are mixed inside the cylindrical space between the die holder and mandrel and which is in front of the die, so both resins are sufficiently mixed inside this cylindrical space before reaching the extrusion hole in the die, thus making it possible to increase the bonding strength in the transition section. The cylindrical space is the space formed between the inner surface of the hole formed in the die holder for inserting the mandrel and the outer surface of the cylindrical shaped mandrel. This cylindrical space improves the mixing action, as well as makes it possible to reduce the joint-flow volume, thus making it possible to shorten the length of the transition section.

Furthermore, this invention provides an apparatus for manufacturing stiffness-taper tubing comprising a die having an extrusion hole, a die holder for holding this die, and a mandrel that is mounted in this die holder and which fits inside the extrusion hole; and where there are a plurality of resin-supply ports in the die holder from which resins having differing stiffness are switched and supplied to the mandrel in order to form tubing such that the stiffness changes gradually and continuously in the longitudinal direction, and furthermore where the insertion hole for the mandrel connects with the extrusion hole in the die holder and the mandrel is mounted inside this insertion hole, and the plurality of resin-supply ports open up to the cylindrical space that is formed between the inner surface of the mandrel insertion hole and the outer surface of the mandrel, at a position that is separated by a distance from the extrusion hole in the die, and a plurality of resins flow together inside this cylindrical space.

With this structure, a location is formed in the cylindrical space for mixing both resins, and in this space it is possible to obtain suitable mixing action, as well as it is possible to shorten the distance to the supply ports for both resins, making it possible to reduce the amount of residual resin that exists at the time of switching, and suppress any changes or deterioration in quality of the resin due to heating of the residual resin.

In a preferred form, the mandrel inside the mandrel insertion hole is a multiple-thread screw, and the screw grooves are divided into a plurality of positions by forming the screw such that the threads, which form the screw grooves, stop part way and then new threads start from an adjacent offset position.

With this structure, each thread groove of the multi-thread screw (screw with two or more threads) is divided part way, and the resins in the grooves are intricately mixed together to break down simple surface contact between both resins and to form a dispersed mixed state which increases the bonding strength.

BEST MODE FOR CARRYING OUT THE INVENTION

The preferred embodiments of the present invention are explained with reference to the drawings.

Figure 1:
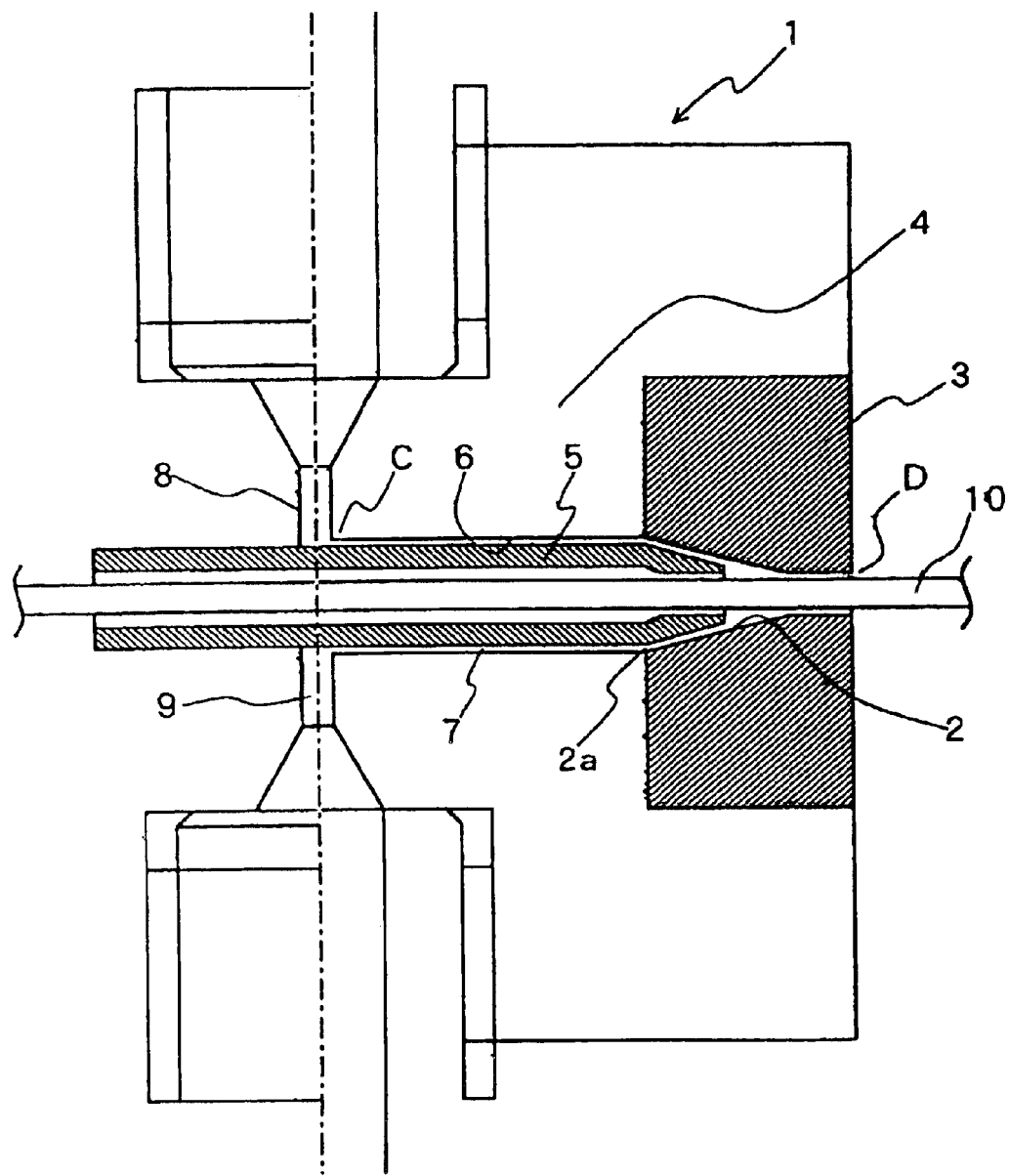
FIG. 1 is a schematic diagram of the stiffness-taper tubing manufacturing apparatus of an embodiment of the present invention.

FIG. 1 is a schematic diagram explaining the stiffness-taper tubing of an embodiment of the present invention.

The extrusion-type formation apparatus 1 of this stiffness-taper tubing manufacturing apparatus comprises; a die 3 having an extrusion hole 2, a die holder 4 which holds this die 3, and a mandrel 5 that is mounted inside this die holder 4. The mandrel 5 is inserted into a mandrel insertion hole 6 that is formed in the die holder 4 and held by the die holder 4. The tip of the mandrel 5 fits inside a conical inlet 2a of the die 3. A cylindrical space 7 is formed between the outer surface of the mandrel 5 and the inner surface of the mandrel insertion hole 6, and the inner surface of the conical inlet 2a on the extrusion hole 2.

A supply port for resin A 8 and a supply port for resin B 9 open up to this cylindrical space 7. In addition, the position where these resin supply ports 8, 9 open up to the cylindrical space 7 is the aforementioned mixing point C for the resins, and the outlet of the extrusion hole 2 of the die 3 is the discharge point D. The joint-flow volume V between these points C, D can be made very small because the diameter of the cylindrical space 7 is small and the width of the space is thin. In this way, it is possible to reduce the time required for replacement when switching resins and shorten the length of the transition section.

When forming stiffness-taper tubing, first only resin A (the first resin) is supplied from the resin A supply port 8, and the resin A section is formed using only resin A. When doing this, the resin is discharged from the extrusion hole 2 while pulling out a core member 10 that is inserted in the center of the mandrel 5, and tubing with an inner diameter that corresponds to the diameter of the core member 10 is formed. Next, supplying of resin A stops, and only resin B (the second resin) is supplied from the resin B supply port 9.

At this time, the previous joint-flow volume V, including the cylindrical space 7 in the die holder 4, is already filled with resin A. From this state, resin A is gradually replaced with resin B. As resin B moves into the cylindrical space 7 it replaces resin A. The volume of this cylindrical space is very small so, as described above, it is possible to reduce the time required for replacement and shorten the length of the transition section.

The transition section, where the resins A and B are mixed by way of the cylindrical space 7, is formed in this way, and after all of resin A has been replaced by resin B in the cylindrical space 7, the resin B section is formed with only resin B. In this way, the stiffness-taper tubing is formed by extrusion.

In this cylindrical space 7, it is possible to add a means for actively mixing the resins while they flow. By doing so it is possible to form a mixed section where the simple contact state between the resins is broken down and the resins are uniformly mixed, and thus it is possible to improve the bonding strength. This kind of mixing means is described later.

Moreover, in the embodiment shown in FIG. 1, the resin supply ports 8, 9 are close to the supply sources of the resins so while one resin is being supplied, the volume of the other resin that remains decreases, so any possibility of changes in quality or deterioration due to heating of the residual resin decreases, making it possible to obtain high-quality extrusion tubing.

The mandrel 5 is depicted in the figure as a single cylindrical member that is long in the axial direction, however, it is possible for the tip to be removable such that it can be replaced with a tip that fits the shape of conical inlets 2a of various kinds of dies 3.

Also, when switching between resins A and B, it is possible to switch from resin A to resin B by gradually reducing the amount of resin A that is supplied while gradually increasing the amount of resin B that is supplied in order to keep the total supplied amount of both resins constant.

Figure 2:
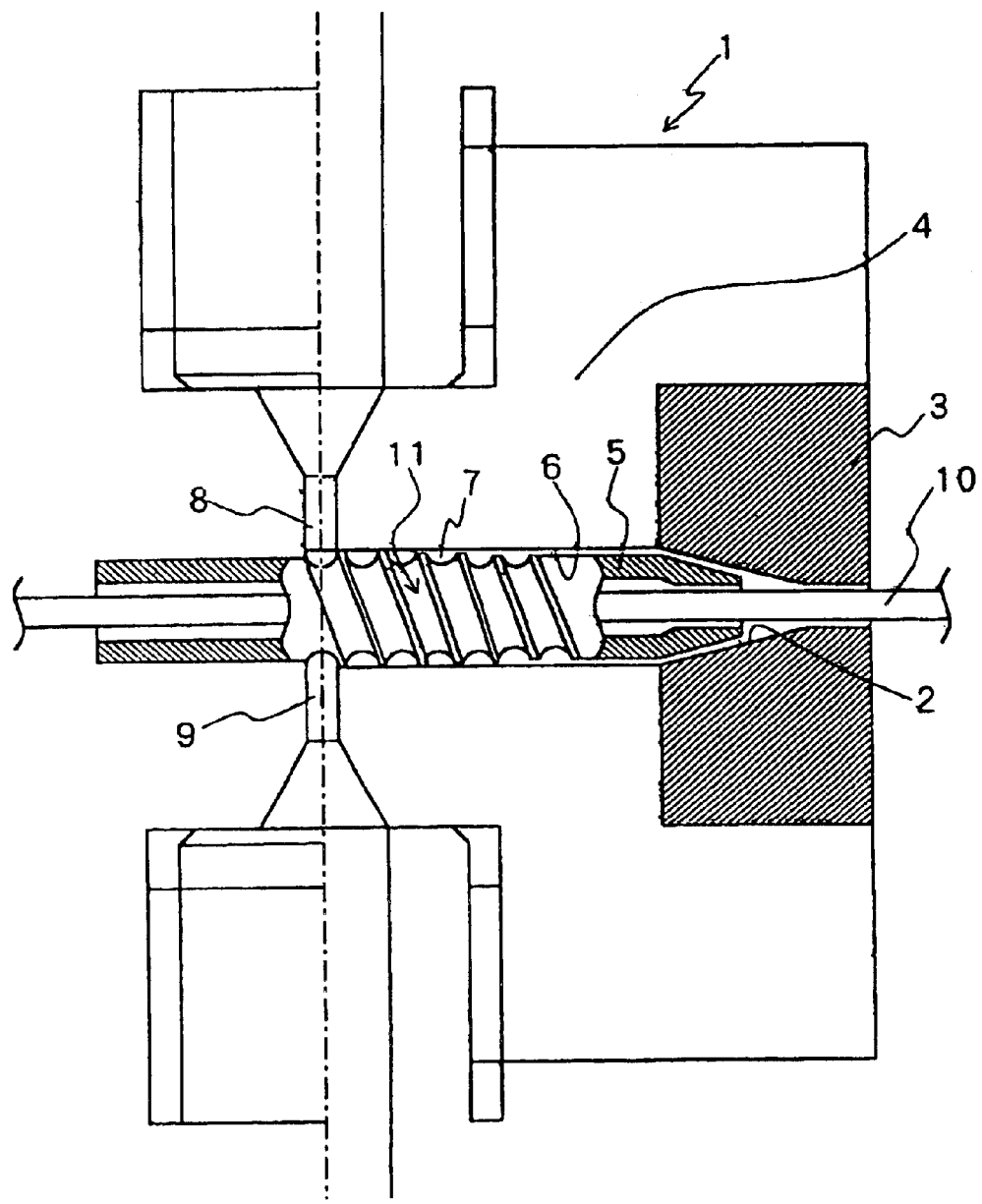
FIG. 2 is a schematic diagram of another embodiment of the invention.

FIG. 2 is a schematic diagram explaining another embodiment of the invention. In this embodiment, there is a means for mixing the resins inside the cylindrical space 7 of the embodiment shown in FIG. 1.

In this embodiment, a multiple-thread screw 11 is formed on the mandrel 5 as the means for mixing the resins. Each of the supply ports 8, 9 for the resins A, B face and open up to a different adjacent screw groove. The height of the threads gradually becomes lower as the threads advance forward. The resins that are supplied from each of the resin supply ports 8, 9 go over the threads in the axial direction as they gradually wind forward along the respective screw grooves. By doing this both of the resins are actively mixed in the cylindrical space 7 between the inner surface of the mandrel insertion hole 6 and the outer surface of the mandrel 5 (in this embodiment the inside is a screw shape). Through this active mixing, any simple contact between the resins A and B is broken down, and a section where the two resins are uniformly mixed is formed. In this way, the resins are firmly joined in the transition section, and the reliability of the bond is increased. The other construction and effects are similar to those of the embodiment shown in FIG. 1.

Figure 3:
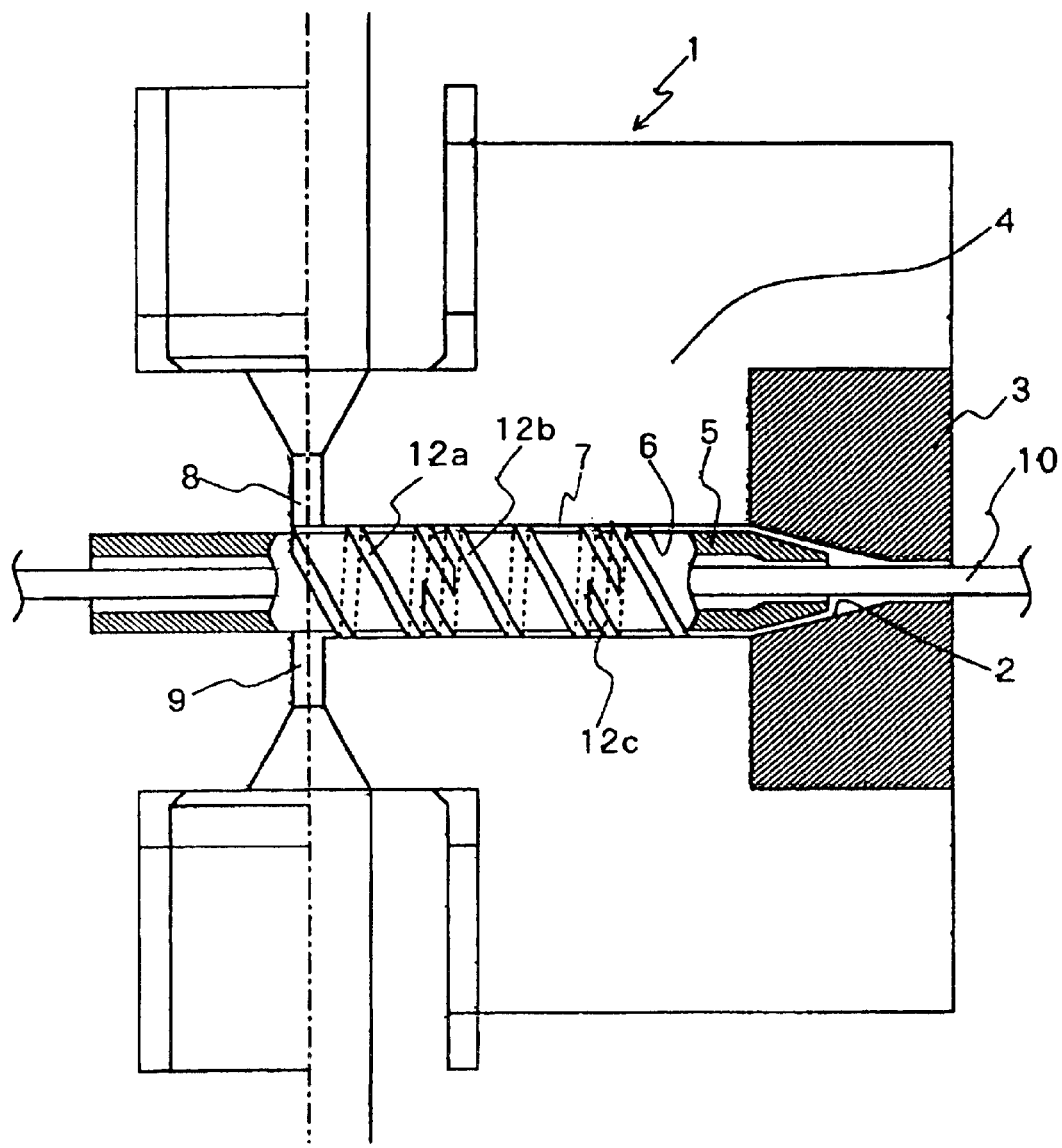
FIG. 3 is a schematic diagram of yet another embodiment of the invention.

FIG. 3 is a schematic diagram explaining yet another embodiment of the invention. This embodiment shows an example of a different means for mixing the resins.

In this embodiment, screws 12a, 12b, and 12c are formed on the mandrel 5 such that the ends of pairs of screw grooves overlap in order. The resin supply ports 8, 9 open up to the same screw groove of the first screw 12a. The supplied resin spirals forward following the threads of the first screw 12a, then moves to the screw groove of the next screw 12b and moves forward, and finally moves to the screw groove of screw 12c and moves forward. By changing screw grooves while moving forward in a spiral motion, it is possible to improve the mixing action of the resins when switching between resins. In this case, the height of the threads may gradually become lower as the threads advance forward in the same way as in the embodiment shown in FIG. 2. The other construction and effects are similar to those of the embodiment shown in FIG. 2.

In each of the embodiments described above, the mixing action can be further improved by rotating the mandrel 5.

Moreover, the number of kinds of resins used in forming the tubing is not limited to two kinds, and it is possible to use three or more kinds of resin.

Figure 4:
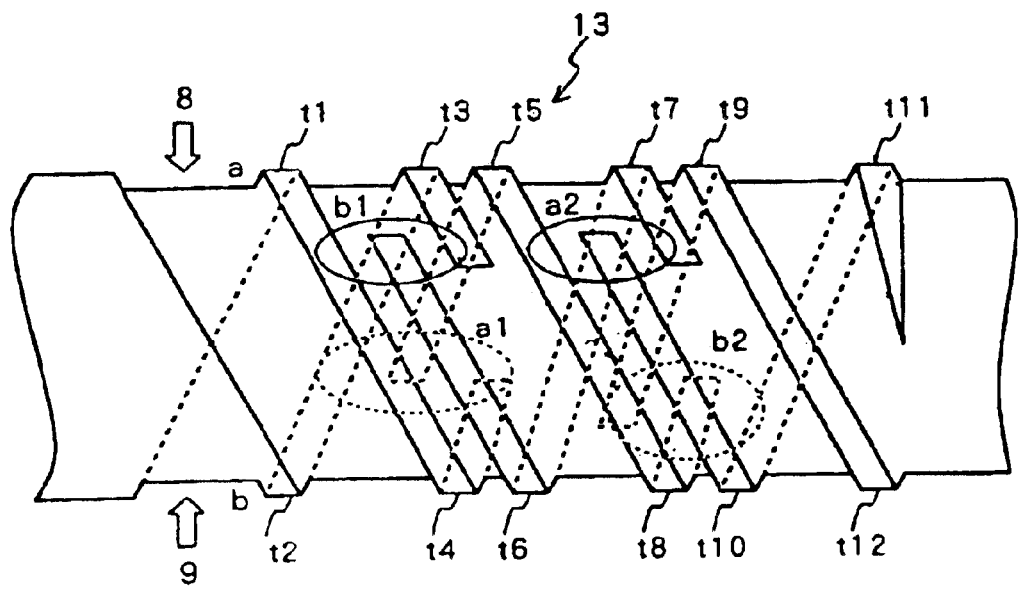
FIG. 4 is a schematic diagram of still yet another embodiment of the invention.
Figure 5:
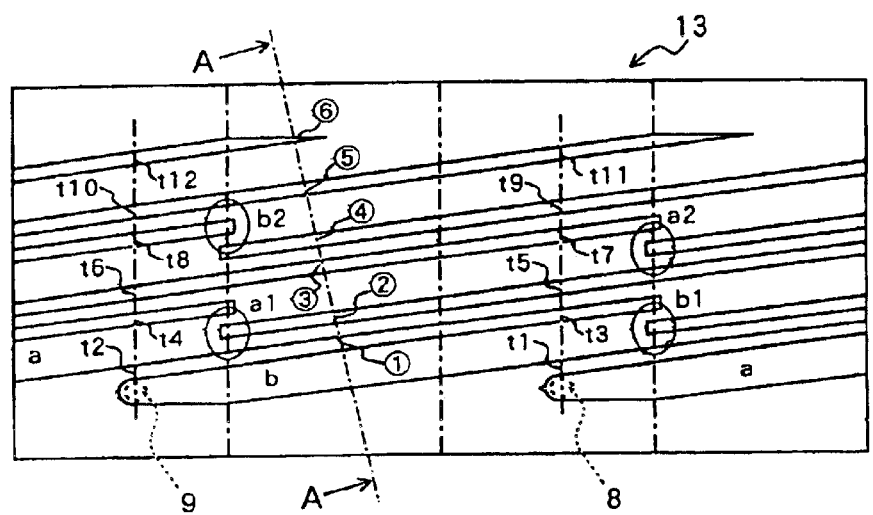
FIG. 5 is an expanded drawing of the embodiment in FIG. 4.
Figure 6:
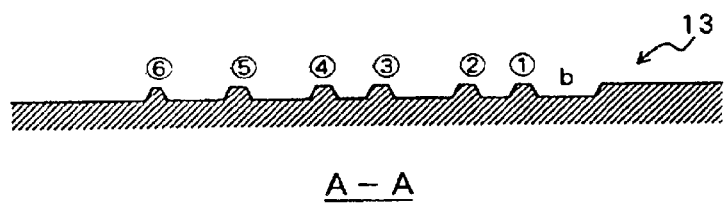
FIG. 6 is a cross-sectional view of section A—A in FIG. 5.
Figure 7:
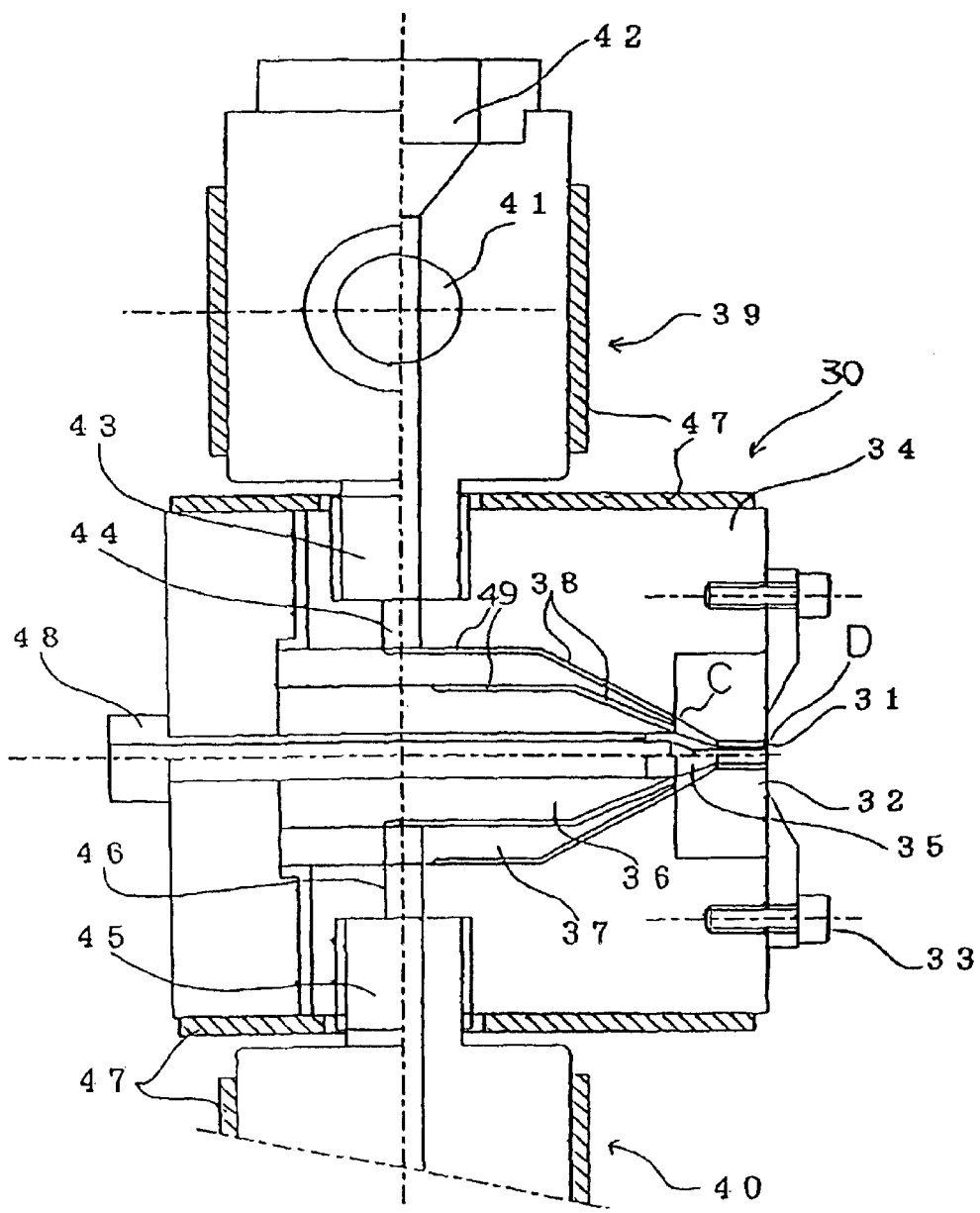
FIG. 7 is a schematic diagram of the prior two-layer extrusion-type formation apparatus.

FIG. 4 is still another embodiment of the invention. This embodiment is an example of changing the screw section of the mandrel. FIG. 5 is an expanded drawing of the embodiment and FIG. 6 is a cross-sectional view of the section A—A in FIG. 5.

The mandrel 13 of this embodiment (only the screw section is shown) is an example of the mandrel 5 shown in FIG. 2 in which the multiple-thread screw has been changed. Facing each starting portion of the screw groove 'a' and the screw groove 'b', the supply port 8 of the first resin (resin A) and the supply port 9 of the second resin (resin B) open up from the die holder 4 (see FIG. 2), respectively. The screw groove 'a' is divided into two by a thread 't5' at a point of division 'a1'. In other words, at this point of division 'a1', the screw thread 't4' stops part way, and there is a new screw thread 't5' that is formed adjacent to it. The screw groove 'a' is divided in this way.

Similarly, screw groove 'b' is divided into two by a screw thread 't6' at the point of division 'b1'. The divided multiple-thread screw is further divided into two in a similar manner at points of division 'a2' and 'b2'. As can be seen from the figure, the screw threads, 't1', 't3', 't5', ..., 't11' that are evenly spaced from the supply port 8 in the axial direction, are opposite from threads 't2', 't4', 't6', ..., 't12' that are evenly spaced from the supply port 9, and are such that threads 't1' and 't4', 't3' and 't2', 't5' and 't8', 't7' and 't6', 't9' and 't12' and 't11' and 't10' are connected. Also, screw threads (1) to (6) in cross-section A—A are connected to the threads 't3', 't5', 't7', 't9', 't11' and 't12'.

By feeding the resins through these screw grooves that have been repeatedly divided in this way, both resins are intricately mixed at the interface when switching between resin A and resin B, thus breaking down the state of surface contact and dispersing the resins such that they are mixed uniformly or almost uniformly. The embodiment described above is of a double thread screw, but it is also possible to use a triple-thread or other multiple-thread screw.

INDUSTRIAL APPLICABILITY

As explained above, in this invention, the previous and later resins are adequately mixed when switching between and extruding in order the different resins, so the bonding strength in the A transition section is high and there is no possibility of the bond coming apart, thus it is possible to obtain highly reliable stiffness-taper tubing. In other words, by extruding and replacing the resin while mixing the resins in the transition section, the resins are mixed uniformly with no inclined surfaces or wedge-shaped surface contact in the interface between the resins, so the bonding strength between the resins is increased.

Moreover, the volume of the mixed space after the different resins are mixed until they are discharged from the die is reduced, making it possible to shorten the length of the transition section. Furthermore, the volume of residual resin that is waiting for the resin to be switched is reduced, and therefore it is possible to suppress any change in quality or deterioration due to heating of the resin, making it possible to obtain high-quality stiffness-taper tubing.

When this invention is used particularly as a medical-use catheter, the bond in the transition section between the flexible section on the distal end, that is inserted into the body, and the stiff section at the proximal end becomes strong, so reliability of the medical equipment is increased, and it is possible to obtain a high-quality catheter where the length of the transition section is long enough to maintain the capability of being threaded through arteries while at the same is short enough to improve operability, and where the quality of the resin in the tubing does not deteriorate.

What is claimed is:

1. An apparatus for manufacturing stiffness-taper tubing comprising:

a die having an extrusion hole, a die holder for holding said die, and a mandrel which is mounted inside said die holder and fits in said extrusion hole, and which forms stiffness-taper tubing by switching between and supplying resins having different stiffnesses over said mandrel from a plurality of resin-supply ports that are formed in said die holder such that the stiffness gradually changes in the lengthwise direction, wherein a mandrel insertion hole that connects to said extrusion hole is formed in said die holder and said mandrel is mounted in this mandrel insertion hole, and said plurality of resin-supply ports open up to a cylindrical space that is formed between the inner surface of said mandrel insertion hole and the outer surface of said mandrel at a position that is separated from the extrusion hole in said die, and the plurality of resins flow together in this cylindrical space, and wherein said mandrel in said mandrel insertion hole is formed like a screw having a thread which gradually becomes lower as the thread advances forward.

2. The apparatus for manufacturing stiffness-taper tubing of claim 1, wherein said mandrel in said mandrel insertion hole is a multi-thread screw that is formed such that the screw grooves are divided up at a plurality of positions by forming threads, that form said screw grooves, that stop part way and new threads start at an adjacent offset position, and wherein the height of said threads gradually becomes lower as the threads advance forward.

3. The apparatus for manufacturing stiffness-taper tubing of claim 1 in which said screw has a first thread and a second thread, and wherein an end of the first thread offsets and partially overlaps with an end of the second thread.

* * * * *